United States Patent
Lin et al.

(10) Patent No.: US 7,301,604 B2
(45) Date of Patent: Nov. 27, 2007

(54) METHOD TO PREDICT AND IDENTIFY DEFOCUS WAFERS

(75) Inventors: Chun-Hung Lin, Taoyuan (TW); Louie Liu, Hsin-Chu (TW); Li-Kong Turn, Taichung (TW); Chi-Hung Liao, Sanchong (TW); Ham-Ming Hsieh, Hsin-Chu (TW); Yi-Chang Sung, Jhubei (TW); Hsin-Chun Chiang, Shanhua Township, Tainan County (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 638 days.

(21) Appl. No.: 10/786,495

(22) Filed: Feb. 25, 2004

(65) Prior Publication Data

US 2005/0185170 A1    Aug. 25, 2005

(51) Int. Cl.
   *G01B 11/00*   (2006.01)
   *G03B 27/52*   (2006.01)

(52) U.S. Cl. .......................... 355/55; 355/53; 356/399; 356/401

(58) Field of Classification Search .................. 355/53, 355/55; 356/399–401; 250/548, 201.1; 430/5, 30
See application file for complete search history.

(56) References Cited

U.S. PATENT DOCUMENTS

| | | | |
|---|---|---|---|
| 4,890,239 A * | 12/1989 | Ausschnitt et al. | 430/30 |
| 5,283,141 A * | 2/1994 | Yoon et al. | 430/30 |
| 6,432,829 B2 | 8/2002 | Muller et al. | |
| 6,674,510 B1 * | 1/2004 | Jasper et al. | 355/55 |
| 6,975,407 B1 * | 12/2005 | Wang et al. | 356/601 |

\* cited by examiner

*Primary Examiner*—Sang H. Nguyen
(74) *Attorney, Agent, or Firm*—Duane Morris LLP (57) ABSTRACT

A method and system for identifying a defocus wafer by mapping a topography of each wafer in a first wafer batch using a level sensor apparatus (100); calculating a focus spot deviation (402) from the data, the focus spot deviation (402) corresponding to a height by which a focus spot of a photo exposure module would be defocused by the topography; converting the focus spot deviation (402) to a corresponding wafer stage set point to which the photo exposure module is set, to focus the focus spot on each wafer in the wafer batch; and identifying a defocus wafer in the wafer batch, as a wafer having a topography that would defocus the focus spot, even when the photo exposure module is set to the wafer stage set point.

19 Claims, 6 Drawing Sheets

FOCUS SPOT STATISTICS

| Wafer | Chuck ID | Deviations | | |
|---|---|---|---|---|
| | | X [mm] | Y [mm] | deviation [μm] |
| 1 | 1 | -141.32400 | -7.80000 | 0.542148 |
| 1 | 1 | -126.69160 | -66.64960 | 1.295974 |
| 1 | 1 | -126.69160 | 51.04960 | 0.550704 |
| 1 | 1 | -112.05920 | -66.64960 | 1.506365 |
| 1 | 1 | -68.16200 | -96.07440 | 0.456564 |
| 1 | 1 | -68.16200 | 109.89920 | 0.895035 |
| 1 | 1 | -53.52960 | -125.49920 | 1.113183 |
| 1 | 1 | -53.52960 | 109.89920 | 0.443870 |
| 1 | 1 | -9.63240 | 139.32400 | 0.786096 |
| 1 | 1 | 5.00000 | -125.49920 | 1.681745 |
| 1 | 1 | 63.52960 | 109.89920 | 0.573930 |
| 1 | 1 | 78.16200 | 109.89920 | 1.017531 |
| 1 | 1 | 92.79440 | -96.07440 | 0.922599 |
| 1 | 1 | 107.42680 | 80.47440 | 1.547343 |
| 1 | 1 | 122.05920 | -66.64960 | 0.665561 |
| 1 | 1 | 136.69160 | -37.22480 | 0.404567 |
| 1 | 1 | 136.69160 | -7.80000 | 0.405736 |
| 1 | 1 | 136.69160 | 21.62480 | 0.503105 |
| 2 | 2 | -141.32400 | -7.80000 | 0.543358 |
| 2 | 2 | -126.69160 | -66.64960 | 1.231986 |
| 2 | 2 | -126.69160 | 51.04960 | 0.542519 |
| 2 | 2 | -112.05920 | -66.64960 | 1.486671 |
| 2 | 2 | -82.79440 | 109.89920 | 0.778743 |
| 2 | 2 | -68.16200 | -125.49920 | 0.523200 |
| 2 | 2 | -68.16200 | -96.07440 | 0.488616 |
| 2 | 2 | -68.16200 | 109.89920 | 0.812353 |
| 2 | 2 | -53.52960 | -125.49920 | 1.139583 |

METHOD TO PREDICT AND IDENTIFY DEFOCUS WAFERS

FIELD OF THE INVENTION

The invention relates to a manufacturing process performed on semiconductor wafers, and more particularly, to a manufacturing process based on surface topography of a semiconductor wafer.

BACKGROUND

In a semiconductor fab, during a photo exposure process step, a photo exposure module in a scanner focuses electromagnetic energy on a focus spot that focuses on a semiconductor wafer surface. The scanned wafer surface is made to be smooth and planar for precise positioning at the focal plane, or focus, of the scanner. The wafer surface is polished by CMP, chemical mechanical planarization, to make a smooth, planar polished surface on the wafer.

Following CMP, on the planarized wafer surface, the surface topography includes a range of taller topography features and a range of shorter topography features, of micrometer step height changes. When the taller topography features (or shorter topography features) are present in sufficient numbers to dominate the surface topography, they defocus the focus spot. The height amount that defocuses the focus spot is referred to as, a deviation amount, also referred to as a focus deviation, and also referred to as, a focus spot deviation (FSD). The photo exposure module has a wafer stage set point that will need adjustment according to the FSD to adjust the focus spot into focus on the wafer surface.

A process for determining the focus spot deviation will now be described. The wafer topography of a batch of wafers is mapped, and the mapped information is analyzed to calculate the FSD. The FSD is a relative height measure by which the focus spot would be defocused due to the height variations of the wafer topography. Then, the FSD sets a wafer stage set point for the photo exposure module. The photo exposure module is set to the wafer stage set point, which adjusts the height of the focus spot to correctly focus on successive wafers of the wafer batch. Thus, a new wafer stage set point is determined by the measure of the FSD. The batch of wafers are processed by the photo exposure module that has been adjusted to the new set point. However, the batch of wafers may have a wafer with an actual topography that would cause defocus of the focus spot, even after the photo exposure module has been adjusted to a new wafer stage set point by the amount of the FSD. Such a wafer in the batch is referred to as a defocus wafer. Thus, a defocus wafer in the batch has a topography that would need to be processed according to a wafer stage set point that is different from the permissible value of the calculated FSD that determines the wafer stage set point. Processing a defocus wafer similarly as the other wafers in the same wafer batch, would reduce the yield of the wafer batch. Thus, a need exists for an invention to identify a defocus wafer and prevent it from being processed with a defocused focus spot. Further a need exists for an invention to dynamically readjust the wafer stage set point with a corrected focus of the focus spot for processing a defocus wafer.

Prior to the invention, the wafer topography was measured by a highly accurate measuring apparatus called a level sensor apparatus, LS. The LS measured topography peak height variations per unit of surface area. According to an algorithm, an FSD was calculated using the LS measurements. The calculated results were recorded in a real time monitor (RTM) process control chart for the FSD. Prior to the invention, multiple process control charts were required. Since wafer fabrication involves a stack of successive planarized layers, the thicker the layer stacks, the bigger the value of FSD becomes. Thus, each of the successive planarized layers needed a separate RTM process control chart for focus spot deviation. Further, no RTM process chart could set a sole criteria to predict or to catch a defocus wafer.

In a photo exposure module, its wafer stage set point is determined according to the following procedure. First, level sensor apparatus measurements are taken of the topography of the wafers in a first wafer batch. Then, by applying statistics, a statistical measurement of the topography is obtained. That statistical measurement is analyzed to calculate a focus spot deviation. The process control chart is updated with the focus spot deviation. Then, the photo exposure module is adjusted to a wafer stage set point, as determined by the focus spot deviation. Then the batch of wafers are processed by the photo exposure module that has been adjusted to the new wafer stage set point.

Before the next succeeding batch of wafers are processed by the photo exposure module, new level sensor apparatus measurements are taken of their topography, to obtain a new focus spot deviation for updating the process control chart. In this manner, as the wafer topography changes from batch to batch due to process variations from batch to batch, the photo exposure module is adjusted to a new wafer stage set point. Thus, the photo exposure module adjusts to the changes in wafer topography from batch to batch. One drawback of the existing system, is that one or more wafers in a processing batch are defocus wafers, which are wafers that have greater focus spot deviations than can be compensated by the new wafer stage set point. It would be advantageous to identify the defocus wafers before they become processed by the photo exposure module. Then the photo exposure module can be readjusted with a corrected wafer stage set point that focuses the focus spot on the defocus wafer. By readjusting the wafer stage set point to process a defocus wafer, the production yield of the processed batch is desirably increased.

SUMMARY OF THE INVENTION

The invention is a method of dynamic focus spot deviation obtained by a new algorithm that precisely captures, i.e., identifies a defocus wafer for a scanner, such as, a 12" AT Twin-Stage (or triple stage) Scanner. The method identifies a defocus wafer by obtaining a difference between a wafer stage set point and a corrected wafer stage set point based on an actual measurement of wafer topography.

According to the invention, a method for identifying a defocus wafer, includes and is not limited to the steps of:

collecting data by mapping a topography of each wafer in a first wafer batch;

calculating a focus spot deviation from the data, the focus spot deviation corresponding to a height by which a focus spot of a photo exposure module would be defocused by the topography;

updating a process control chart with the focus spot deviation;

converting the focus spot deviation to a corresponding wafer stage set point to which the photo exposure module is set, to focus the focus spot on each wafer in a present or current wafer batch; and identifying a defocus wafer in the present or current wafer batch, as a wafer having a topography that would defocus the focus spot, even when the photo exposure module is set to the wafer stage set point that corresponds with the focus spot deviation.

An advantage is that no defocus wafer is missed. Anther advantage is that the method is capable of identifying a large number of defocus wafers. Another advantage is that the method prevents low yield processing of successive wafer batches due to defocus wafers. Another advantage is that the method eliminates a separate RTM process control chart for each successive layer on a substrate.

According to an embodiment of the invention, the method further includes resetting the photo exposure module to a corrected wafer stage set point to focus the focus spot on the defocus wafer.

According to a further embodiment of the invention, the method further includes; photo exposing the topography of the defocus wafer by the photo exposure module that is reset to the corrected wafer stage set point.

According to another embodiment of the invention, the method further includes, resetting the photo exposure module to a corrected wafer stage set point to focus the focus spot on the defocus wafer, during a process of photo exposing the topography of the wafers in the next succeeding batch by the photo exposure module; and photo exposing the topography of the defocus wafer by the photo exposure module that is reset to a corrected wafer stage set point.

Further, the invention is a method of identifying a wafer as a defocus wafer and providing a gating signal to activate a complementary feedback defocus gating mechanism of the photo exposure module. The complementary feedback defocus gating mechanism is used to reset the photo exposure module to a corrected wafer stage set point, to focus the focus spot on the defocus wafer. According to an embodiment of the invention, the method further includes, supplying the focus spot deviation as a wafer gating signal identifying the defocus wafer to a gating mechanism of the photo exposure module. An advantage is that no RTM process control chart is required for gating a defocus wafer.

Further, the invention is a method that performs dynamically as a supplement to dynamic performance of M/C. An advantage is that the method quickly verifies dynamic performance of M/C.

According to another embodiment of the invention, the set point for a control chart is set by a process control chart, by the steps of; calculating an updated focus spot deviation that corresponds to a height by which a focus spot of a photo exposure module would be defocused by the topography of the wafers in the next succeeding batch; and updating the process control chart with the updated focus spot deviation. The invention further relates to a method of using a level sensor apparatus according to the method steps of;

scanning the topography of each wafer in a next succeeding wafer batch with the level sensor apparatus to obtain scan data in the form of height measurements per unit area of each wafer in the next succeeding wafer batch;

identifying a defocus wafer by its scan data;

resetting the photo exposure module to a corrected wafer stage set point to focus the focus spot on the defocus wafer, during a process of photo exposing the topography of the wafers in the next succeeding batch; and photo exposing the topography of the defocus wafer by the photo exposure module that is reset to a corrected wafer stage set point.

A defocus wafer has a topography with Z-axis heights that recur with sufficient frequency that they will defocus the focus spot during a scan. In the scanning equipment, the wafer stage position is adjustable in height, to compensate for wafers that become thicker in height as more layers of semiconductor materials are built up on the wafer. Further, the wafer stage position can be adjusted in height to compensate for the defocus caused by the Z-axis heights of wafer topography. Then, the wafer surface is correctly positioned at the focal plane of the scanner equipment, which correctly positions the wafer surface at the focal plane of the scan.

The invention processes large numbers of wafers to catch defocus wafers in real time.

DETAILED DESCRIPTION

Figure 1:
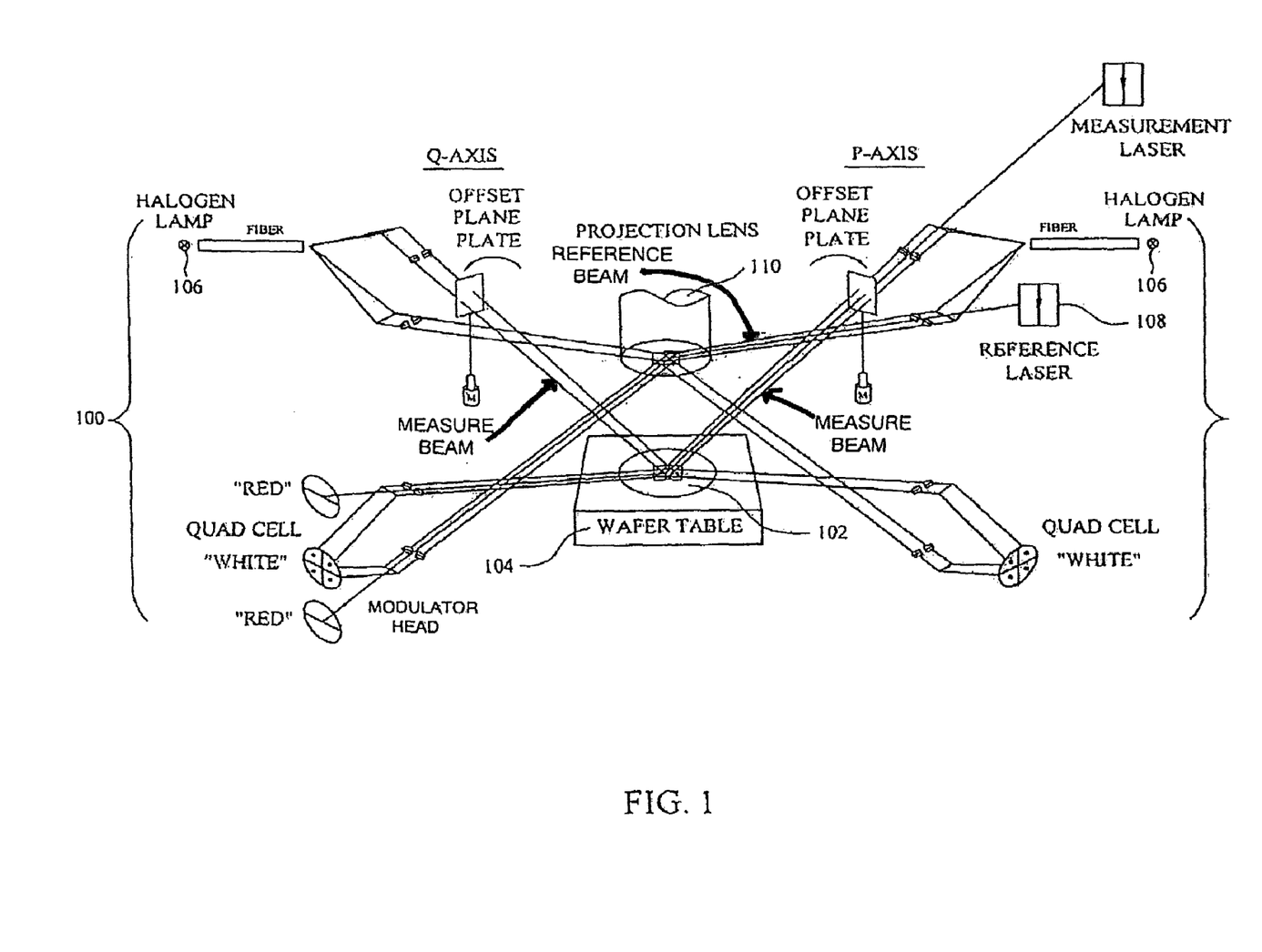
FIG. 1 is a diagrammatic view of a level sensor apparatus.

FIG. 1 discloses a level sensor apparatus (100), known in the technical field of semiconductor fabrication, for mapping a topography of a semiconductor wafer (102) mounted on a wafer table (104). The level sensor apparatus (100) includes a light sources from halogen lamps (106) and a collimated beam from a reference laser (108) supplied to a projection lens (110). The topography of the wafer (102) is scanned by the apparatus (100) to collect data by mapping a topography of each wafer in a wafer batch. The data consists of measurements of wafer surface topography height Z at X-Y coordinates. The wafer topography of a batch of wafers is mapped, and the mapped information is analyzed to calculate the focus spot deviation, FSD. The FSD is a relative height measure by which the focus spot would be defocused due to the height variations of the wafer topography.

Figure 2:
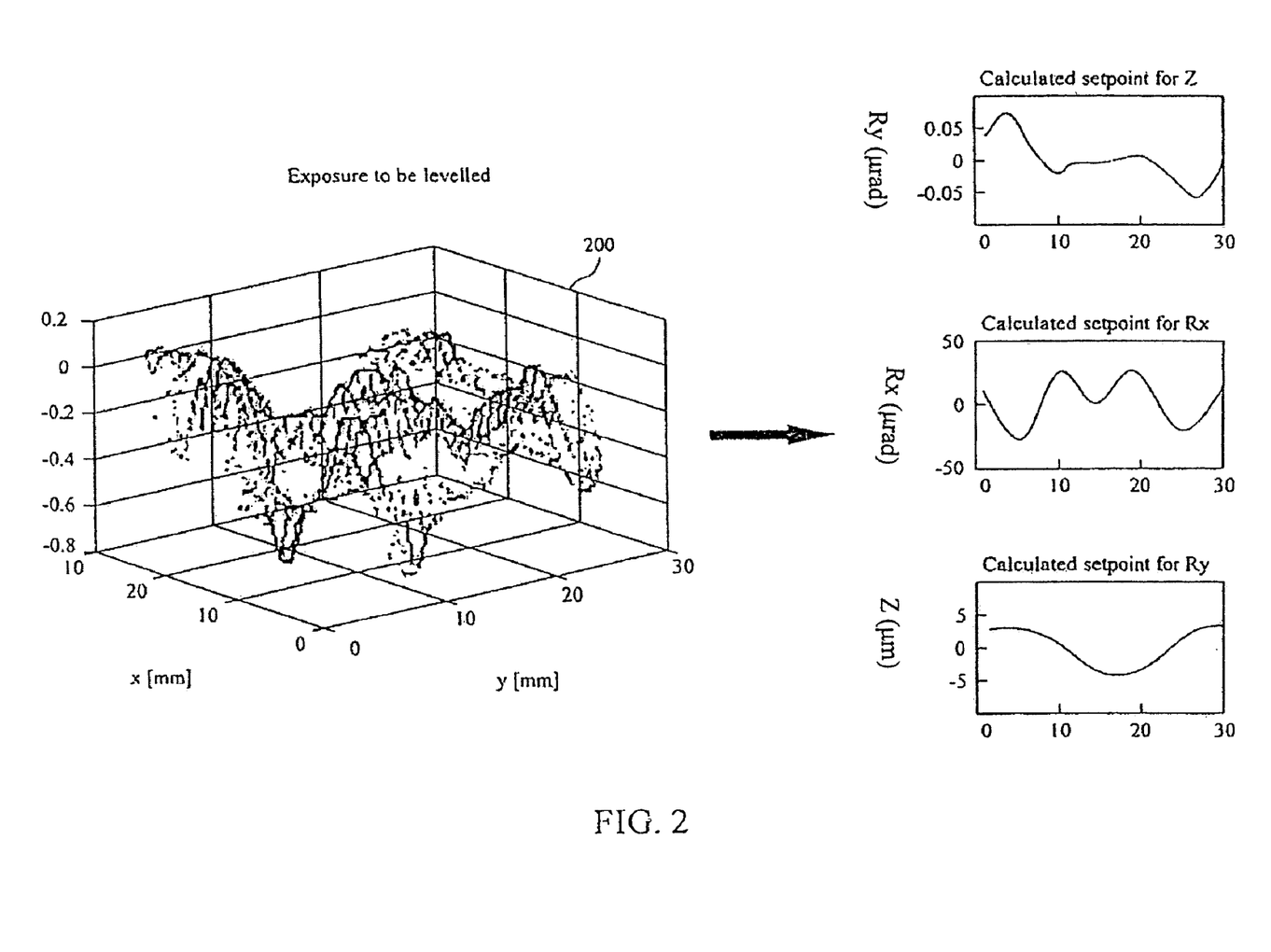
FIG. 2 is a three dimensional map of a wafer surface, together with respective graphs of calculated set points along three axes.

FIG. 2 discloses a graph (200) of mapping information data, which records measurements of wafer surface topography height Z at X-Y coordinates. The mapping information collectively produces statistics that are the basis for statistical calculation of set points for Rx, Ry and Z in micrometers. These set points correspond to a focus spot deviation corresponding to a height by which a focus spot of an industry known, photo exposure module would be defocused by the topography of the wafers in the wafer batch.

Figure 4:
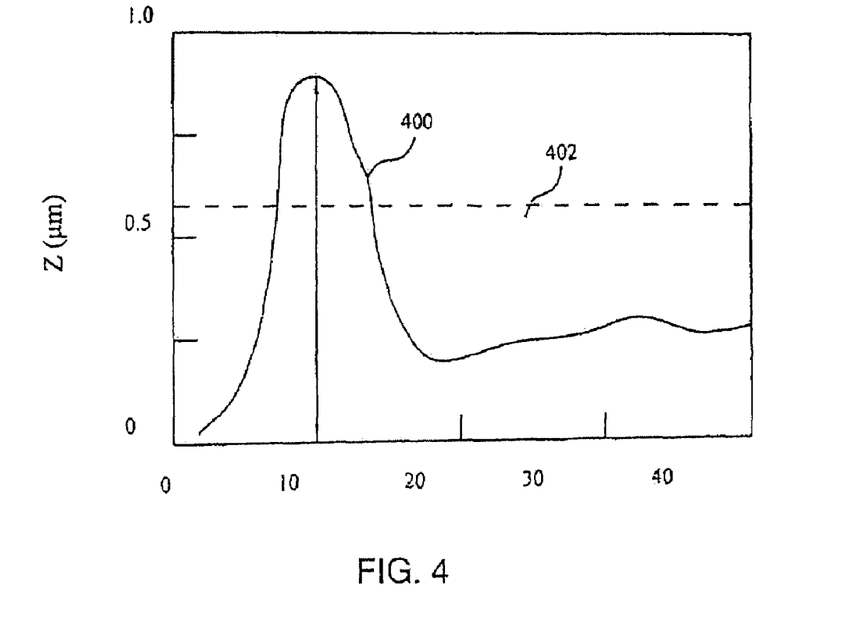
FIG. 4 is a graph of a frequency distribution of focus spot deviations from which is calculated a static focus spot deviation that corresponds to a wafer stage set point to which the photo exposure module is set, to focus the focus spot on a wafer in a wafer batch.

FIG. 4 discloses a graph (400) of a frequency distribution of focus spot deviations from which is calculated a static focus spot deviation (402). The focus spot deviation (402) is converted to a wafer stage set point to which the photo exposure module is set, to correct for the defocus, and to focus the focus spot on each wafer of the wafer batch. Thus, the FSD (402) sets a wafer stage set point for the photo exposure module. The photo exposure module is set to the wafer stage set point, which adjusts the height of the focus spot to correctly focus on successive wafers of the wafer batch. Thus, a new wafer stage set point is determined by the measure of the FSD (402). The batch of wafers can be processed by the photo exposure module that has been adjusted to the new set point. However, the batch of wafers may have a wafer with an actual topography that would defocus of the focus spot, even when the photo exposure module is adjusted to a new wafer stage set point that corresponds to the amount of the FSD (402). Such a wafer in the batch is referred to as a defocus wafer. Thus, a defocus wafer in the batch has a topography that would need to be processed according to a wafer stage set point that is different from the permissible value of the calculated FSD (402) that determines the wafer stage set point. Processing a defocus wafer similarly as the other wafers in the same wafer batch, would reduce the yield of the wafer batch.

According to a further drawback, the wafer is fabricated by successive build up of layers. The thicker the layers, the higher are the corresponding focus spot deviation values. Higher focus spot deviation values allow defocus wafers to be missed and contribute to lower manufacturing yields.

Before the next succeeding batch of wafers are processed by the photo exposure module, new level sensor apparatus measurements are taken of their topography, to obtain a new focus spot deviation for updating the process control chart. In this manner, as the wafer topography changes from batch to batch due to process variations from batch to batch, the photo exposure module is adjusted to a new wafer stage set point. Thus, the photo exposure module adjusts to the changes in wafer topography from batch to batch. One drawback of the existing system, is that one or more wafers in a processing batch are defocus wafers, which are wafers that have greater focus spot deviations than can be compensated by the new wafer stage set point. It would be advantageous to identify the defocus wafers before they become processed by the photo exposure module. Then the photo exposure module can be readjusted with a corrected wafer stage set point that focuses the focus spot on the defocus wafer. By readjusting the wafer stage set point to process a defocus wafer, the production yield of the processed batch is desirably increased.

Figure 5:
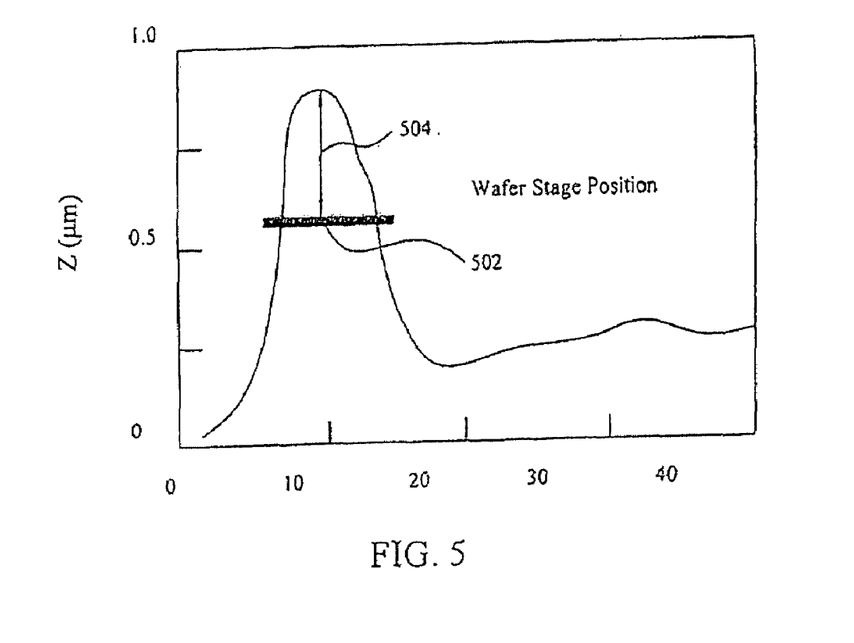
FIG. 5 is a graph similar to FIG. 4, and further disclosing a corrected wafer stage set point to which a photo exposure module is set to focus a focus spot on a defocus wafer.

FIG. 5 discloses a graph (500) wherein, the invention produces a dynamic focus spot deviation (504) calculated as the topography height as actually measured and shown by the graph (500), minus the wafer stage set point (502) that is the same as the static focus spot deviation (402) of FIG. 4, to determine the real focus spot for processing a wafer, especially for processing a defocus wafer. The invention catches defocus wafers by a dynamic focus spot deviation method.

Figure 3:
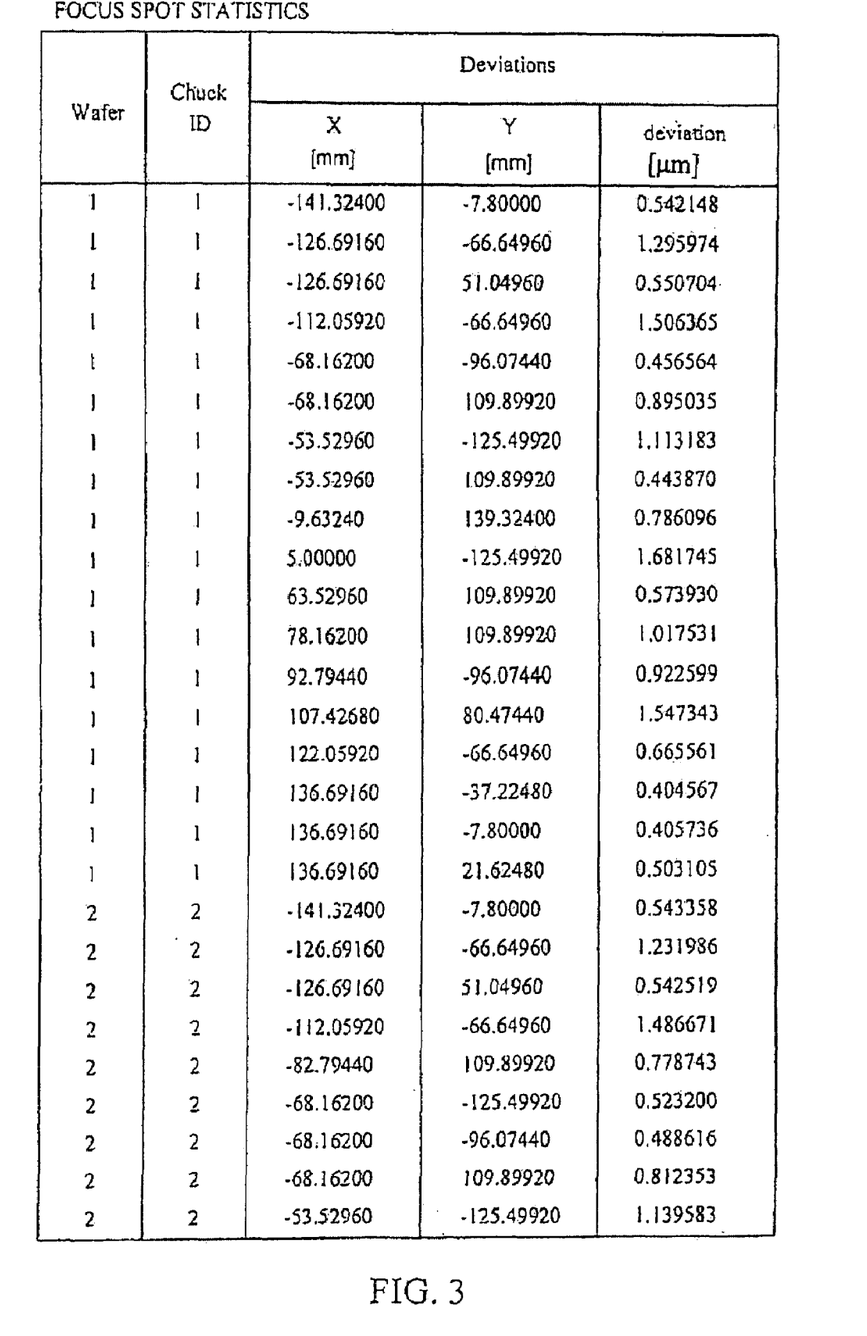
FIG. 3 is a portion of a database having columns of X-axis and Y-axis coordinates for a corresponding to a Z-axis wafer height measurement, and another column of focus spot deviations along the Z-axis

According to the invention, a method for identifying a defocus wafer involves, colleting data by mapping a topography of each wafer in a first wafer batch. According to an embodiment of the invention, the level sensor apparatus (100) maps the topography. The method further involves, calculating a focus spot deviation (402) from the data, the focus spot deviation (402) corresponding to a height by which a focus spot of a photo exposure module would be defocused by the topography. According to an embodiment, a data base (300) disclosed by FIG. 3 has internal algorithms assigned to columns of the data base (300), which calculate the focus spot deviation (402). For example, the focus spot deviation (402) is calculated as a standard deviation from the highest frequency of topography height measurements recorded in the graph (400). Further, the method involves, identifying a defocus wafer as a wafer having a topography that would defocus the focus spot, even when the photo exposure module is set to the wafer stage set point that corresponds with the focus spot deviation (402). According to an embodiment, the method further involves, identifying the defocus wafer by its scan data in the form of height measurements per unit area of topography. According to a further embodiment, the method further involves, resetting the photo exposure module to a corrected wafer stage set point (504) to focus the focus spot on the defocus wafer. According to a further embodiment, the method further involves, resetting the photo exposure module to a corrected wafer stage set point (504) to focus the focus spot on the defocus wafer, during a process of exposing the topography of the wafers by the photo exposure module, and photo exposing the topography of the defocus wafer by the photo exposure module that is reset to a corrected wafer stage set point.

Figure 6:
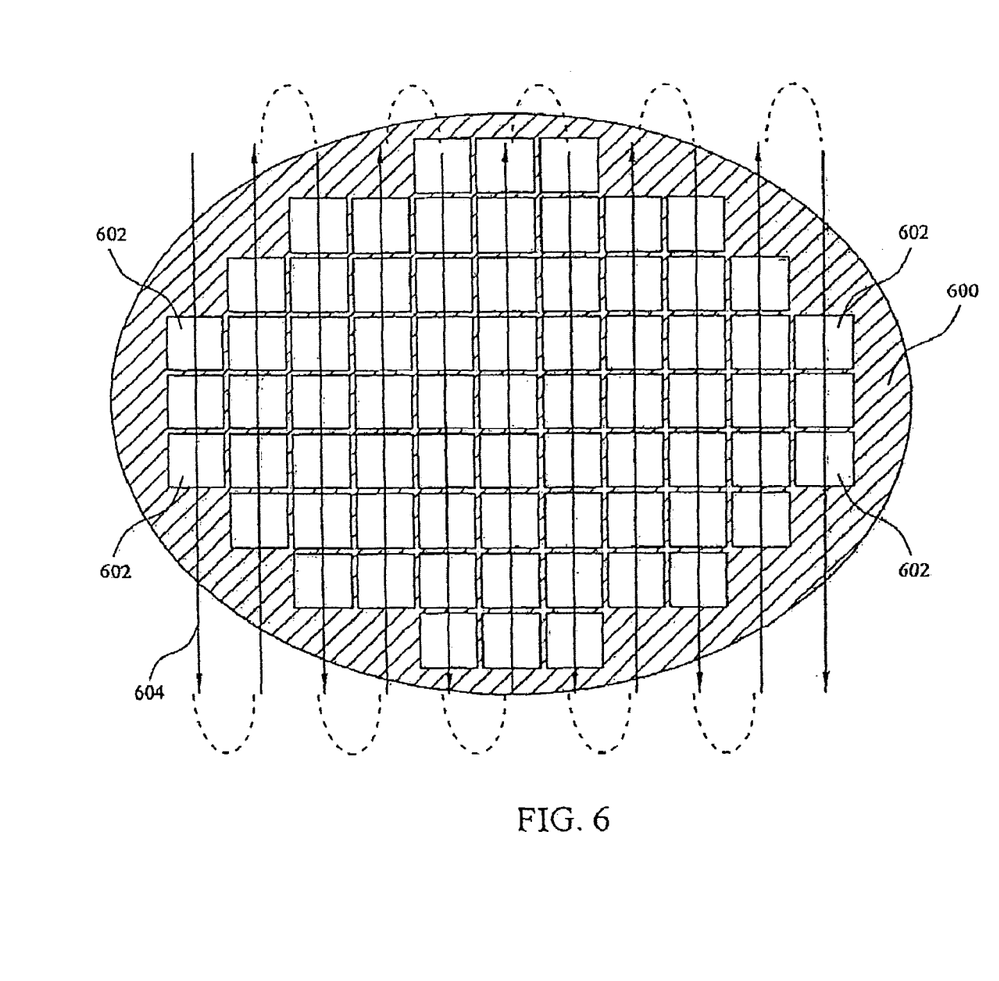
FIG. 6 is a top view of a wafer having semiconductor dies, and further disclosing an axis of a scanning path for a level sensor apparatus.
Figure 7:
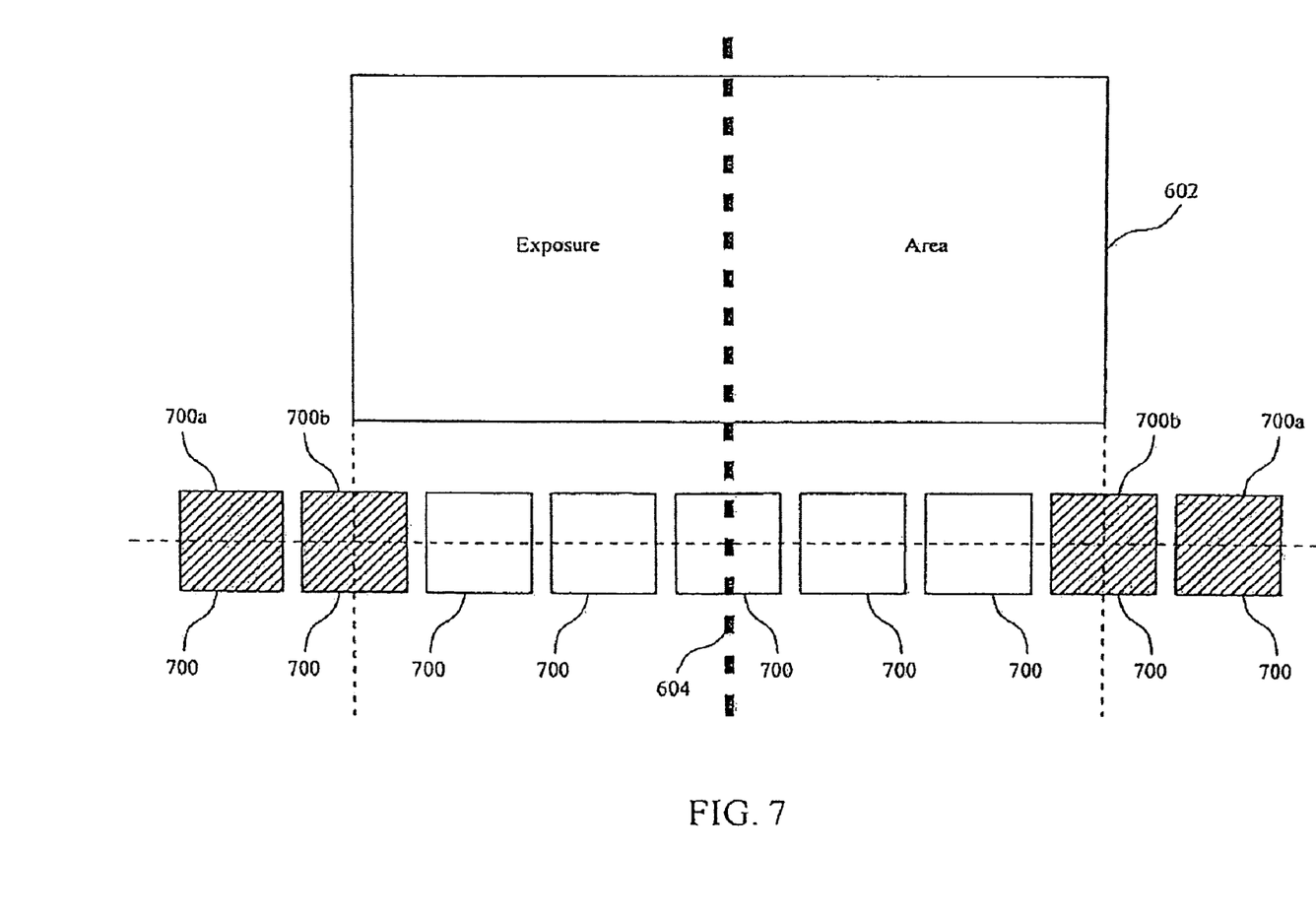
FIG. 7 is a diagram of multiple sensors of a level sensor apparatus and the exposure area being scanned by the apparatus.

FIG. 6 discloses a wafer (600) having multiple semiconductor dies (602) defining regions of semiconductor circuit elements, which are covered by photo resist material. The photo resist material is to be patterned by exposure to a patterned beam of an industry known photo exposure module. FIG. 6 further discloses an axis (604) of a scanning path for the level sensor apparatus (100). FIG. 7 discloses multiple rectangular sensors (700) on the level sensor apparatus (100). The central sensor (700) is aligned on the axis (604) during scanning. An exposure area of a corresponding semiconductor die (602) is depicted as being scanned. However, only the central five sensors (700) will scan solely the semiconductor die (602). The outermost sensors (700a) will not scan any part of the semiconductor die (602). Accordingly, the data collected by the sensors (700a) will not be selected for calculating the focus spot deviation. Similarly, the data collected by the sensors (700b) will not be selected, because the sensors (770b) partially scan a region outside of the semiconductor die (602). Thus, only the data mapped by the sensors (700) that scan wholly within the region of the semiconductor die (602) are selected for calculating the focus spot deviation.

According to another embodiment of the invention, the dynamically obtained focus spot deviation is supplied to a complementary feedback defocus gating mechanism of the level sensor apparatus (100).

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for identifying a defocus wafer, comprising the steps of:
    collecting data by mapping a topography of each wafer in a first wafer batch;
    calculating a focus spot deviation from the data, the focus spot deviation corresponding to a height by which a focus spot of a photo exposure module would be defocused by the topography;
    updating a process control chart with the focus spot deviation;
    converting the focus spot deviation to a corresponding wafer stage set point to which the photo exposure module is set, to focus the focus spot on each wafer in a present or current wafer batch; and
    identifying a defocus wafer in the present or current wafer batch, as a wafer having a topography that would defocus the focus spot, even when the photo exposure module is set to the wafer stage set point that corresponds with the focus spot deviation.

2. The method of claim 1, further comprising the step of:
    resetting the photo exposure module to a corrected wafer stage set point to focus the focus spot on the defocus wafer.

3. The method of claim 1, further comprising the steps of:
    resetting the photo exposure module to a corrected wafer stage set point to focus the focus spot on the defocus wafer; and
    photo exposing the topography of the defocus wafer by the photo exposure module that is reset to the corrected wafer stage set point.

4. The method of claim 1, further comprising the steps of:
resetting the photo exposure module to a corrected wafer stage set point to focus the focus spot on the defocus wafer, during a process of photo exposing the topography of the wafers in the next succeeding batch by the photo exposure module; and
photo exposing the topography of the defocus wafer by the photo exposure module that is reset to a corrected wafer stage set point.

5. The method of claim 4, further comprising the step of:
calculating an updated focus spot deviation that corresponds to a height by which a focus spot of a photo exposure module would be defocused by the topography of the wafers in the next succeeding batch; and
updating the process control chart with the updated focus spot deviation.

6. The method of claim 1, further comprising the step of:
supplying the focus spot deviation as a wafer gating signal identifying the defocus wafer to a gating mechanism of the photo exposure module.

7. The method of claim 1, further comprising the steps of:
scanning the topography of each wafer in the first wafer batch to obtain scan data in the form of height measurements per unit area of each wafer in the first wafer batch; and
calculating the focus spot deviation from the scan data.

8. The method of claim 1, further comprising the steps of:
scanning the topography of each wafer in the first wafer batch with a level sensor apparatus to obtain scan data in the form of height measurements per unit area of each wafer in the first wafer batch;
assembling the scan data in a database; and
calculating the focus spot deviation from the scan data.

9. The method of claim 1, further comprising the steps of:
scanning the topography of each wafer in the present or current wafer batch to obtain scan data in the form of height measurements per unit area;
identifying the defocus wafer by its scan data; and
resetting the photo exposure module to a corrected wafer stage set point to focus the focus spot on the defocus wafer.

10. The method of claim 1, further comprising the steps of:
scanning the topography of each wafer in the present or current wafer batch with a level sensor apparatus to obtain scan data in the form of height measurements per unit area;
identifying the defocus wafer by its scan data; and
resetting the photo exposure module to a corrected wafer stage set point to focus the focus spot on the defocus wafer.

11. The method of claim 1, further comprising the steps of:
scanning the topography of each wafer in the next succeeding wafer batch to obtain scan data in the form of height measurements per unit area of each wafer in the next succeeding wafer batch;
identifying the defocus wafer by its scan data;
resetting the photo exposure module to a corrected wafer stage set point to focus the focus spot on the defocus wafer, during a process of photo exposing the topography of the wafers in the next succeeding batch; and
photo exposing the topography of the defocus wafer by the photo exposure module that is reset to a corrected wafer stage set point.

12. The method of claim 11, further comprising the step of:
calculating an updated focus spot deviation that corresponds to a height by which a focus spot of a photo exposure module would be defocused by the topography of the wafers in the next succeeding batch; and
updating the process control chart with the updated focus spot deviation.

13. The method of claim 1, further comprising the steps of:
scanning the topography of a photo resist material covering patterned dies on the wafers in the present or current wafer batch to obtain scan data in the form of height measurements per unit area;
identifying the defocus wafer by its scan data; and
resetting the photo exposure module to a corrected wafer stage set point to focus the focus spot on the defocus wafer.

14. The method of claim 13, further comprising the steps of:
scanning the topography of the photo resist material covering the patterned dies with a scanner having multiple sensors; and
obtaining valid scan data only when all of the multiple scanning sensors simultaneously cover the patterned dies.

15. The method of claim 14, further comprising the steps of:
calculating an updated focus spot deviation corresponding to a height amount by which a further wafer batch would defocus the focus spot;
updating the process control chart with the updated focus spot deviation.

16. A system for identifying a defocus wafer, comprising:
a level sensor creating mapping data of a topography of each wafer in a first wafer batch;
a process control chart updated with a focus spot deviation calculated from the mapping data, the focus spot deviation corresponding to a height by which a focus spot of a photo exposure module would be defocused by the topography;
a photo exposure module set to a corresponding wafer stage set point corresponding to the focus spot deviation, to focus the focus spot on each wafer in a present or current wafer batch; and
means for identifying a defocus wafer in the present or current wafer batch, as a wafer having a topography that would defocus the focus spot, even when the photo exposure module is set to the wafer stage set point that corresponds with the focus spot deviation.

17. The system of claim 16, wherein, the photo exposure module is resettable to a corrected wafer stage set point to focus the focus spot on the defocus wafer.

18. The system of claim 16, wherein, the level sensor has multiple topography scanners.

19. The system of claim 16, wherein, the topography each wafer corresponds to the topography of patterned dies on each wafer.

* * * * *